United States Patent
Oleson et al.

(10) Patent No.: US 10,617,156 B2
(45) Date of Patent: *Apr. 14, 2020

(54) ELECTRONIC HOUSING AND SENSOR CONNECTION ARRANGEMENT

(71) Applicant: Under Armour, Inc., Baltimore, MD (US)

(72) Inventors: Mark A. Oleson, Baltimore, MD (US); Samuel J. Hollenbach, Baltimore, MD (US); F. Grant Kovach, Baltimore, MD (US); Jason Berns, Baltimore, MD (US)

(73) Assignee: Under Armour, Inc., Baltimore, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/252,121

(22) Filed: Jan. 18, 2019

(65) Prior Publication Data
US 2019/0150527 A1  May 23, 2019

Related U.S. Application Data

(60) Continuation of application No. 14/823,797, filed on Aug. 11, 2015, now Pat. No. 10,251,430, which is a
(Continued)

(51) Int. Cl.
*A41D 1/00* (2018.01)
*A61B 5/00* (2006.01)

(52) U.S. Cl.
CPC ............ *A41D 1/005* (2013.01); *A61B 5/6804* (2013.01); *A61B 5/6823* (2013.01); *A61B 2560/045* (2013.01)

(58) Field of Classification Search
CPC . A41D 1/005; G06F 19/3481; G06F 19/3487; G06F 19/3431; G06F 19/363;
(Continued)

(56) References Cited

U.S. PATENT DOCUMENTS

| 3,534,727 | A | 10/1970 | Roman |
|---|---|---|---|
| 6,571,115 | B2 | 5/2003 | Axelgaard et al. |

(Continued)

FOREIGN PATENT DOCUMENTS

| CN | 202566376 U | 12/2012 |
|---|---|---|
| FR | 2912637 A1 | 8/2008 |

OTHER PUBLICATIONS

Partial European Search Report in EP12186306.

*Primary Examiner* — Brandi N Hopkins
(74) *Attorney, Agent, or Firm* — Maginot, Moore & Beck LLP

(57) ABSTRACT

A garment comprising a sensor, a body portion, a receptacle provided on the body portion, and an electronics module positioned in the receptacle. The receptacle comprises a receptacle housing, a sensor lead, and a receptacle contact. The receptacle housing forms a socket including a back wall and at least one sidewall. The sensor lead abuts the receptacle contact and is retained within a channel extending through the at least one sidewall. The receptacle contact includes a contact surface exposed to the socket with the contact surface oriented substantially perpendicular to the back wall of the socket. The electronics module is releasably positioned within the socket and includes at least one module contact. The at least one module contact abuts the receptacle contact and is electrically connected to the sensor lead when the electronics module is positioned within the socket.

20 Claims, 7 Drawing Sheets

Related U.S. Application Data division of application No. 13/629,207, filed on Sep. 27, 2012, now Pat. No. 9,119,594.

(60) Provisional application No. 61/539,687, filed on Sep. 27, 2011.

(58) Field of Classification Search
CPC ..... G06F 19/3418; H04L 69/16; H04L 67/12; A61B 5/7214; A61B 5/0002; A61B 5/0537; A61B 5/11; A61B 5/02438; G01S 19/19; G06Q 10/0639; H04M 1/7253; H04M 1/72563; A63B 43/00; A63B 24/00; G09B 19/0038; G01D 11/24; G04G 17/08; G04B 37/1413; F16B 21/04
See application file for complete search history.

(56) References Cited

U.S. PATENT DOCUMENTS

| | | | |
|---|---|---|---|
| 6,895,261 B1 | 5/2005 | Palamides | |
| 7,226,321 B2* | 6/2007 | Uhari | G01D 11/24 439/752 |
| 7,428,433 B2* | 9/2008 | Juan | A61B 5/6831 600/390 |
| 7,670,295 B2 | 3/2010 | Sackner et al. | |
| 8,543,195 B1 | 9/2013 | Brockway et al. | |
| 8,792,959 B2* | 7/2014 | Okuda | A61B 5/0408 600/390 |
| 9,775,561 B2* | 10/2017 | Russell | A61B 5/0024 |
| 2005/0107831 A1 | 5/2005 | Hill et al. | |
| 2007/0089800 A1 | 4/2007 | Sharma | |
| 2008/0269579 A1 | 10/2008 | Schiebler | |
| 2009/0047645 A1* | 2/2009 | Dibenedetto | G16H 15/00 434/258 |
| 2009/0048070 A1* | 2/2009 | Vincent | A63B 24/0021 482/8 |
| 2010/0185398 A1 | 7/2010 | Berns | |
| 2010/0292599 A1* | 11/2010 | Oleson | A63B 24/0062 600/519 |
| 2012/0165645 A1 | 6/2012 | Russell et al. | |
| 2013/0077263 A1 | 3/2013 | Oleson et al. | |
| 2014/0189928 A1 | 7/2014 | Oleson et al. | |
| 2015/0119676 A1* | 4/2015 | Okuda | A61B 5/0245 600/388 |
| 2015/0202494 A1 | 7/2015 | Hollenbach | |

* cited by examiner

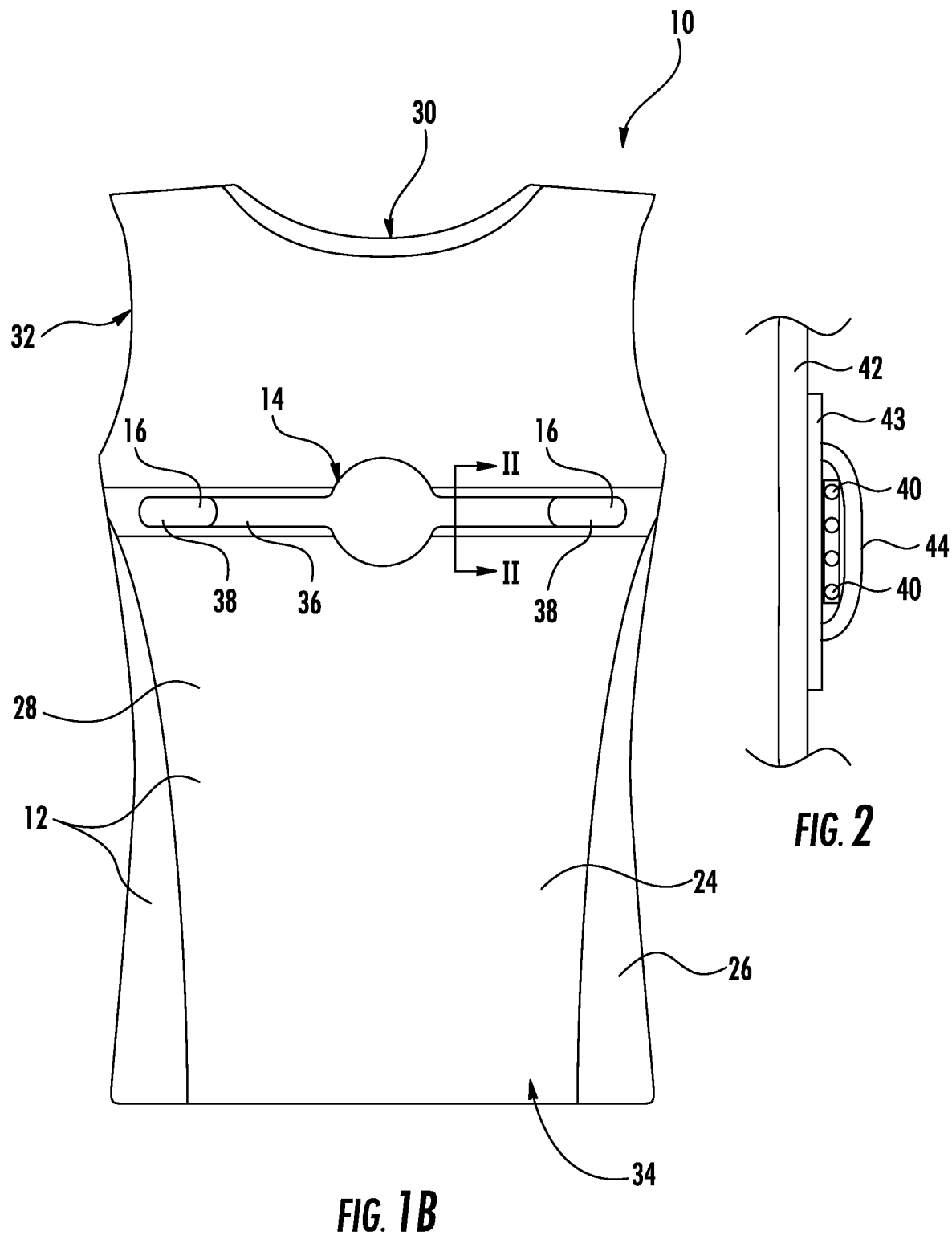

ELECTRONIC HOUSING AND SENSOR CONNECTION ARRANGEMENT

CROSS-REFERENCE TO RELATED APPLICATIONS

This application is a continuation of U.S. patent application Ser. No. 14/823,797, filed Aug. 11, 2015, which is a divisional of U.S. patent application Ser. No. 13/629,207, filed Sep. 27, 2012, now U.S. Pat. No. 9,247,907, which claims priority from U.S. provisional patent application No. 61/539,687, filed Sep. 27, 2011.

FIELD

This application relates to the field of athletic apparel, and particularly to an electronic sensor arrangement on a garment or other an item of apparel.

BACKGROUND

Sensor arrangements are commonly used to monitor various physiological parameters such as heart rate, temperature, breathing rate, etc. These sensor arrangements typically include various electronics components including electrodes, microprocessors, power devices, wired or wireless communications interfaces, display devices, and related housings. While such sensor arrangements are often worn separate from the clothing of the monitored subject, it is increasingly common for such sensor arrangements to be incorporated into the clothing of the test subject. This allows the sensor arrangement to be quickly and conveniently positioned on the test subject for data collection. Placement of sensor arrangements on the garment of the test subject also tends to be more comfortable, as adhesives are not required to attach electrodes and other sensor arrangements to the skin of the test subject.

In sensor arrangements incorporated into articles of apparel, the electronics components are sometimes completely separable from the article of apparel. For example, some watches have included releasable electronics modules configured for placement in a socket provided on a wristband. The electronics module and associated display may then be easily moved to a socket provided on a different device such as an exercise machine. However, when such sensor arrangements with releasable electronics components are incorporated into a garment to be worn on the torso, the resulting arrangement is often bulky and uncomfortable for the wearer. Moreover, the releasable electronics modules are often difficult to connect to or separate from the garment, making use of the sensor arrangement inconvenient for the wearer.

In other sensor arrangements, the electronics components may be inseparable from the garment. For example, some shirts, chest straps or bras include electronics components that are incorporated into the garment such that the components cannot be removed from the garment without destruction of the garment. In these arrangements, critical electronics components such as the microprocessor, power device, and transmitter are potted in a polymer material that is fixed to the garment material. The polymer material seals the electronics components and prevents moisture intrusion. Accordingly, these garments are designed for washing by hand or a machine without destruction of the sensor arrangement provided on the garment. However, in the event of a small imperfection such as a crack or tear in the potting material, moisture may indeed seep into the potting material and short or otherwise destroy the electronics components of the electronics package. Such small imperfections may be the result of a manufacturing defect or wear of the garment and sensor arrangement over time.

In view of the foregoing, it would be desirable to provide a garment or other article of apparel including a sensor arrangement with a releasable electronics module that is comfortable for the wearer. It would be particularly advantageous if such electronics module could be quickly and easily released from or connected to the garment. Furthermore, it would be advantageous if such garment could be repeatedly washed without danger of damaging the sensitive electronics components in the electronics module.

SUMMARY

In accordance with one embodiment of the disclosure, there is provided a garment comprising a sensor, a body portion, a receptacle provided on the body portion, and an electronics module positioned in the receptacle. The receptacle comprises a receptacle housing, a sensor lead, and a receptacle contact. The receptacle housing forms a socket including a back wall and at least one sidewall. The sensor lead abuts the receptacle contact and is retained within a channel extending through the at least one sidewall. The receptacle contact includes a contact surface exposed to the socket with the contact surface oriented substantially perpendicular to the back wall of the socket. The electronics module is releasably positioned within the socket. The electronics module includes at least one module contact. The at least one module contact abuts the receptacle contact and is electrically connected to the sensor lead when the electronics module is positioned within the socket.

Pursuant to another embodiment of the disclosure, there is provided a garment comprising a body portion, an electrode positioned on the body portion, a receptacle positioned on the body portion, and an electronics module releasably positioned in the receptacle. The receptacle comprises a housing, an electrode lead, and a receptacle contact. A first portion of the electrode lead extends through a hole in the electrode, and a second portion of the electrode lead abuts the receptacle contact such that the electrode lead is electrically connected to the receptacle contact. The electronics module includes a module contact that engages the receptacle contact when the electronics module is positioned in the receptacle to establish an electrical connection between the module contact and the receptacle contact.

In accordance with yet another embodiment of the disclosure, there is provided a chest strap comprising an elongated fabric portion, at least one electrode positioned on the elongated fabric portion, a receptacle provided on the chest strap, and an electronics module releasably positioned on the socket. The receptacle comprises a receptacle housing having a rear surface and a front surface with a socket formed in the front surface. The receptacle further comprises at least one electrode lead retained by the receptacle housing. The at least one electrode lead includes a first portion connected to the at least one electrode and a second portion extending through a channel in the receptacle housing. The channel is elongated in a direction that extends parallel to at least a part of the rear surface of the receptacle housing. The electronics module includes at least one module contact that is electrically connected to the electrode lead when the electronics module is positioned within the socket.

The above described features and advantages, as well as others, will become more readily apparent to those of ordinary skill in the art by reference to the following detailed description and accompanying drawings. While it would be desirable to provide a garment with a sensor connection arrangement that provides one or more of these or other advantageous features, the teachings disclosed herein extend to those embodiments which fall within the scope of the appended claims, regardless of whether they accomplish one or more of the above-mentioned advantages.

BRIEF DESCRIPTION OF THE DRAWINGS

FIG. 1B shows a front inside view of the garment of FIG. 1A;

FIG. 2 shows a cross-sectional view of the garment along line II-II of FIG. 1B;

DESCRIPTION

Figure 1A:
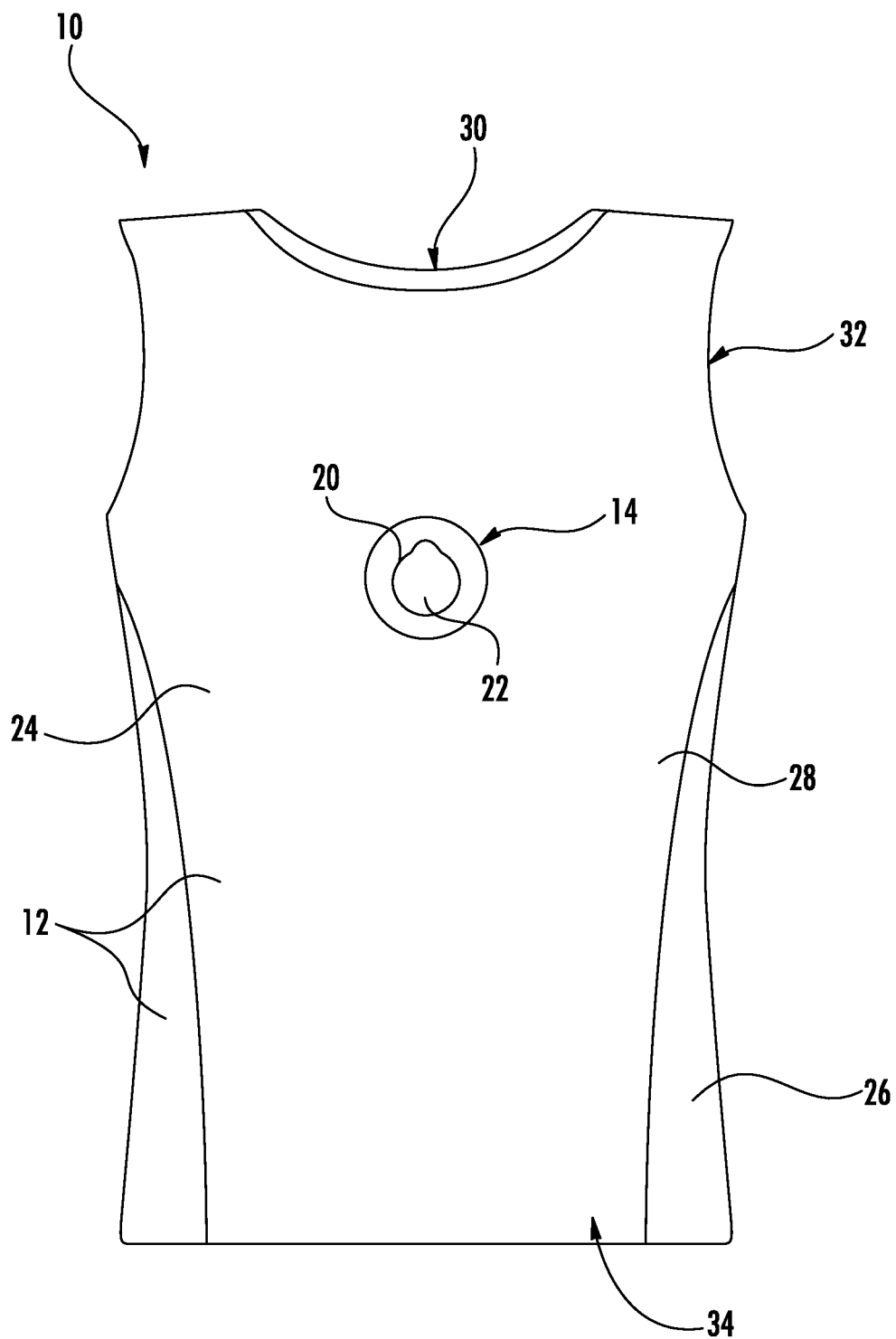
FIG. 1A shows a front outside view of a garment with a sensor arrangement including a releasable electronics module.

With reference to FIGS. 1A and 1B, a garment 10 is comprised of fabric portions 12 with a sensor arrangement 14 attached to one of the fabric portions 12. The sensor arrangement 14 includes electrodes 16 electrically connected to a receptacle 20, with the electrodes 16 and the receptacle 20 bonded to the garment 10 in a non-removable manner. An electronics module 22 is removably connected to the receptacle 20.

The fabric portions 12 of the garment may include a plurality of fabric panels connected together to form the garment. In the embodiment of FIGS. 1A and 1B, the fabric panels include a front panel 24 and a rear panel 26 that together form a torso portion 28 for the garment. The torso portion 28 includes a neck opening 30, arm openings 32, and a waist opening 34. As shown in FIG. 1A, the receptacle 20 of the sensor arrangement 14 is positioned near a central location on the front of the torso portion 28 that corresponds to a location near the heart of a wearer, such as a chest portion of the garment 10. Similarly, as shown in FIG. 1B, the electrodes 16 of the sensor arrangement are positioned on the inside of the torso portion 28 at the chest portion, with the two electrodes 16 located on opposite sides of the receptacle 20.

The electrodes 16 are included on a sensor band 36 that extends laterally along the inside of the torso portion. The electrodes 16 include sensing pads 38 and conductive elements, such as conductive fibers 40 (see FIGS. 2 and 3) that connect the sensor pads 38 to the receptacle 20. As shown in FIG. 1B, the sensing pads 38 are exposed on the interior surface of the garment 10 and are configured to detect electrical signals on the skin of a wearer, such as heart rate or ECG signals, as will be recognized by those of ordinary skill in the art. The sensing pads 38 are connected to the conductive fibers 40 that extend laterally along the sensor band 36 and are configured to deliver electrical signals from the sensing pads 38 to the receptacle 20. The conductive fibers 40 may be any of various electrically conductive elements, including metal wire or electrically conductive textile fibers, such as silver coated elastane fibers.

As shown in FIG. 2, the conductive fibers 40 are generally positioned between an inner fabric layer 42 and an outer fabric layer 44 of the sensor band 36, thus shielding the conductive fibers 40 from electrical noise. Either the inner fabric layer 42 or the outer fabric layer 44 may be provided as a strip of fabric that only covers the sensor band 36, while leaving the inner sensing pads 38 exposed. An intermediate layer 43 may also be positioned between the inner fabric layer 42 and the outer fabric layer 44. However, it will be recognized that various alternative embodiments are also possible. For example, the conductive fibers 40 may be woven or otherwise integrated into a single textile layer on the garment. Furthermore, the layers need not be fabrics or textiles, and in at least one alternative embodiment, one or more of the layers are comprised of a polymer material.

Figure 3:
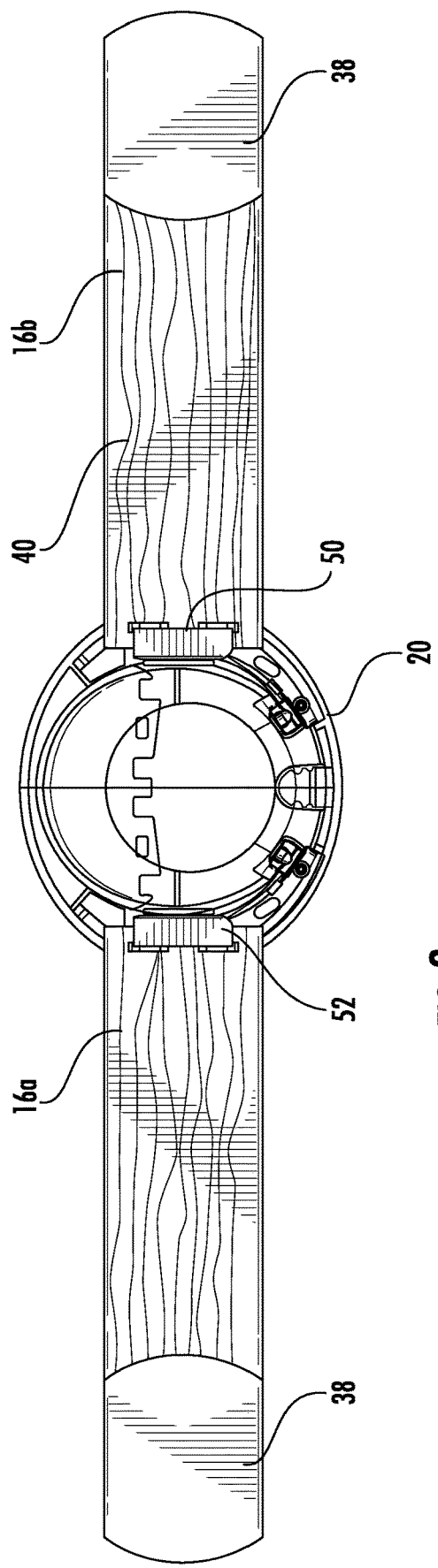
FIG. 3 shows an rear view of a sensor band including receptacle and electrodes in isolation from the garment of FIG. 1B.

FIG. 3 shows a rear view of the electrodes 16 (i.e., a view from inside of the garment 10) with the electrode 16 isolated from the fabric layers 42, 44 of the garment 10. The electrodes 16 include a first electrode 16a and a second electrode 16b positioned on opposite sides of the receptacle 20. Accordingly, the first electrode 16a and the second electrode 16b are electrically separated from one another on the garment 10. A measurable potential difference is thus produced between the first electrode 16a and the second electrode 16b (e.g., an ECG signal which is measured with the electronics components within the electronics module 22).

With continued reference now to FIG. 3, the electrodes 16 are coupled to the rear side of the receptacle 20 via two electrode leads 50 retained within a receptacle housing 70. In particular, the two electrode leads 50 are crimped to the electrodes 16 to establish an electrical connection between the electrodes 16 and the electrode leads 50. The electrodes 16 are coupled to the leads 50 near a middle of the receptacle 20 (i.e., about half way between vertical top and vertical bottom of the receptacle when oriented as shown in FIG. 3). Accordingly, both the electrodes 16 and the leads 50 are centrally located at the side perimeter portions on the rear side of the receptacle housing 70. This arrangement is advantageous for manufacture of the sensor arrangement 14, allowing the electrodes to be easily coupled to the sides of the receptacle 20 without the need to extend further into the receptacle. In the disclosed embodiment, the electrodes only extend a few millimeters past the rear edges of the receptacle housing before they come into contact with the leads 50.

Figure 4:
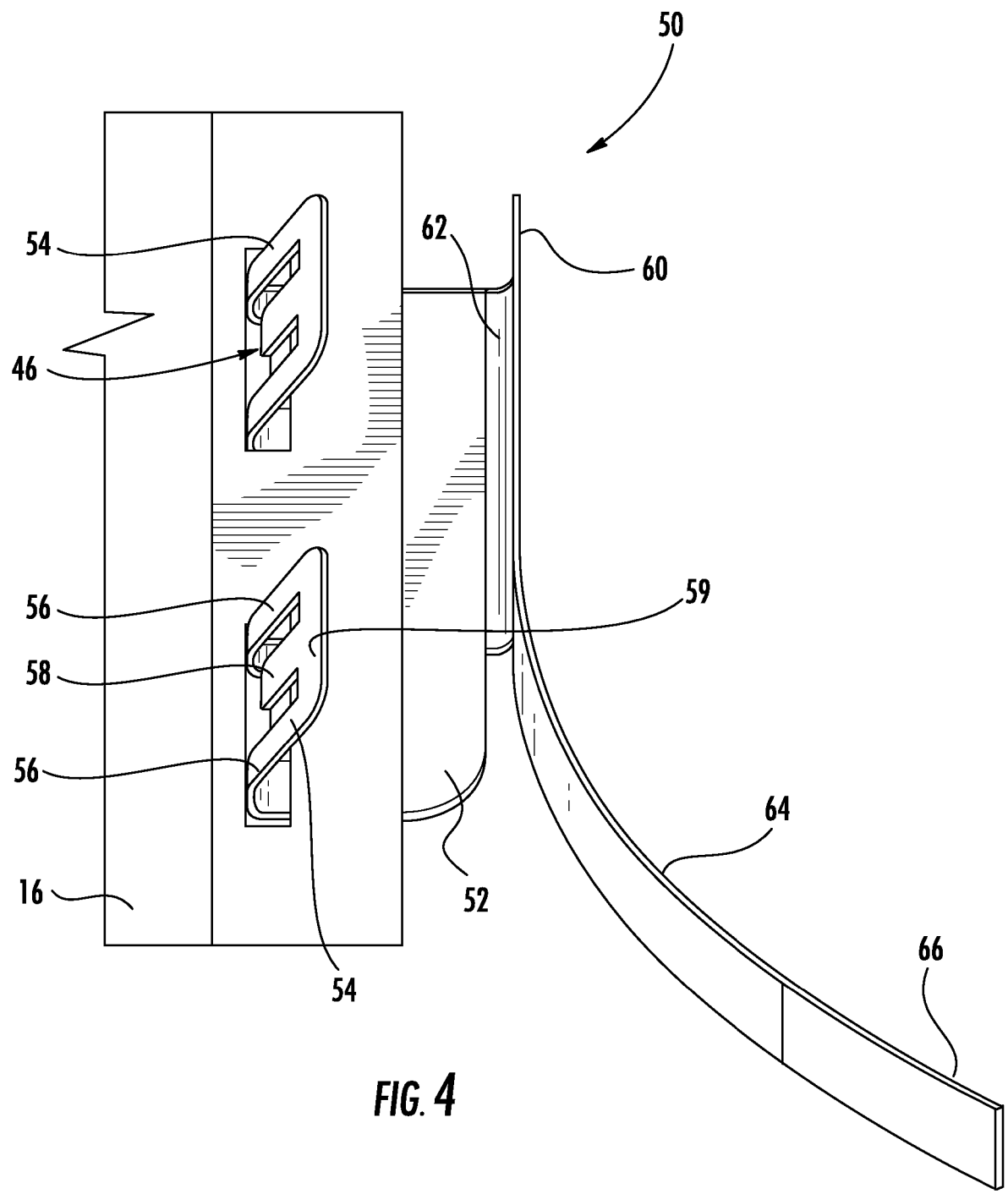
FIG. 4 shows a front perspective view of an electrode lead of the receptacle in engagement with the electrode of FIG. 3.

As best shown in FIG. 4, each electrode lead 50 includes a rear plate 52, two electrode connectors in the form of peripheral tangs 54 extending from one side of the rear plate 52, and a leaf spring 60 extending from the opposite side of the rear plate 52. The two peripheral tangs 54 provide are generally E-shaped members with longer outer arms 56 and a shorter center arm 58 connected along a spine 59. The ends of the longer outer arms 56 are connected to the rear plate 52 and the end of the shorter center arm 58 is free from the rear plate. Each tang 54 extends through a hole 46 in the electrode 16. The longer arms 56 of the tang 54 are bent to an extent that the spine 59 engages the surface of the electrode. In particular, each tang 54 is fastened to the electrode by crimping the tang 54 to the electrode with a strong force during assembly such that the rear plate 52 closely engages the rear surface of the electrode 16 and the E-shaped tangs 54 closely engage the front surface of the electrode 16. As a result, each electrode 16 is fastened to an associated electrode lead 50, and a firm electrical and mechanical connection is established between each electrode 16 and the associated electrode lead 50. Additionally, to further establish a good connection between each electrode 16 and the associated electrode lead 50, in at least one embodiment a thin layer of conductive adhesive is provided between the electrode 16 and the rear plate 52 and/or the tangs 54 of the electrode lead 50. Moreover, although not shown in FIG. 4, the tangs 54 may include sharp edges or other elements to provide for solid and continuous contact to the material forming the electrode 16.

With continued reference to FIG. 4, the leaf spring 60 is provided on an opposite side of the electrode lead 50 from the tangs 54. The leaf spring 60 includes a bend portion 62 with an elongated curved finger 64 extending from the bend portion. The bend portion 62 connects the leaf spring 60 to the rear plate 52 and generally orients the leaf spring 60 about 90° relative to the rear plate 52. The finger 64 flares away from the rear plate 52 as moving toward an end 66 of the finger 64.

Figure 5:
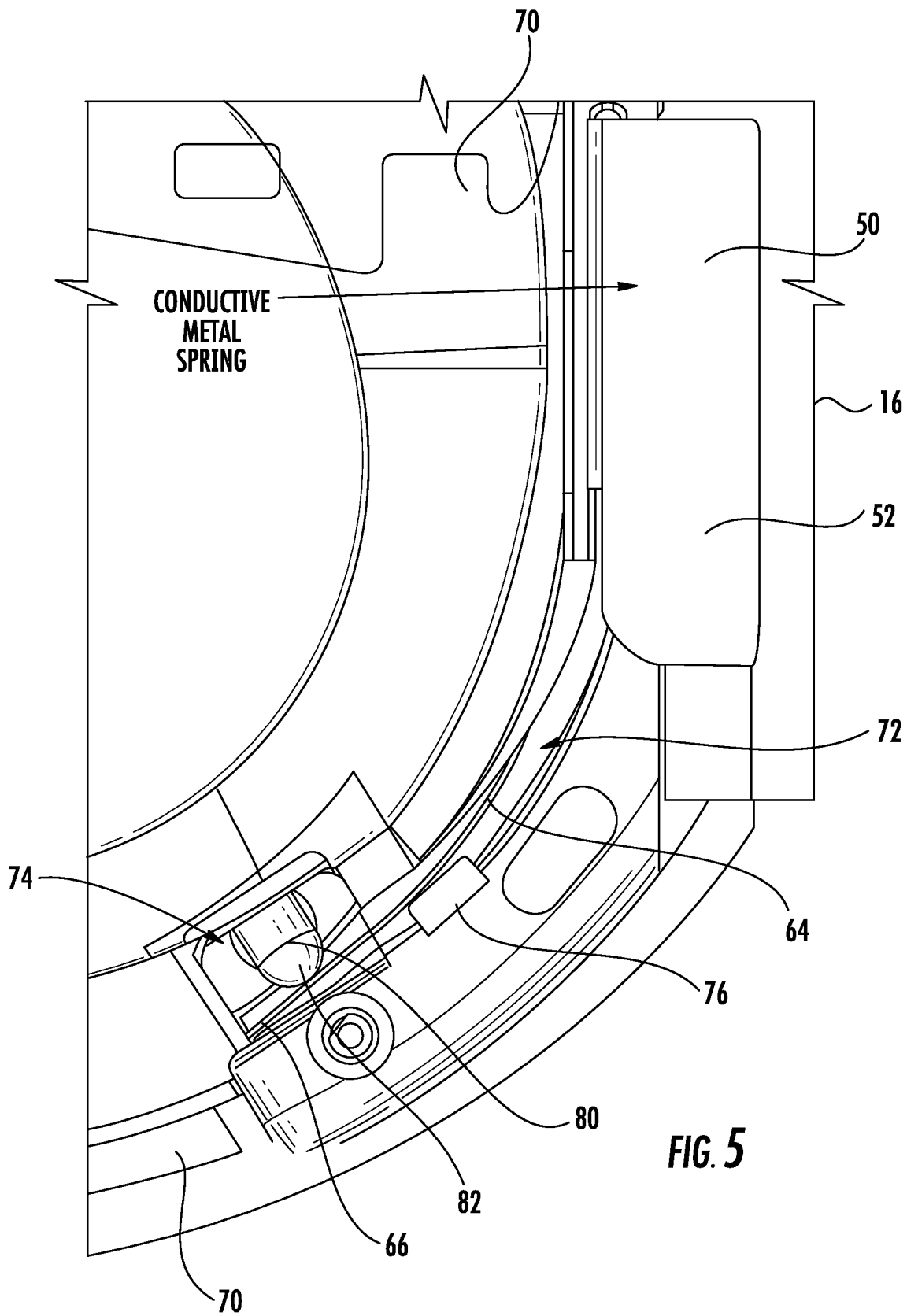
FIG. 5 shows an enlarged rear view of the electrode lead of FIG. 4 positioned in the receptacle.

With reference now to FIG. 5, an enlarged view of the electrode lead 50 is shown positioned in the receptacle housing 70. The receptacle housing 70 generally provides a structure to retain the various components of the receptacle 20, including the electrode leads 50 and receptacle contacts 80 provided by connection pins (also referenced herein as reference numeral 80). The receptacle housing 70 is comprised of a non-conductive, durable and relatively resilient polymer material, such as polyethylene, polypropylene, polyurethane, poly-vinyl chloride or any of various other durable and generally resilient materials.

The rear side of the receptacle housing 70 (as shown in FIGS. 3 and 5) is a substantially flat surface configured to conform to the contours of the wearer's chest, since this rear side faces the body of the wearer. This rear side of the receptacle housing 70 is also bonded to the fabric portions 12 of the garment 10, and particularly the outer surface of the fabric. This bonding may be accomplished using any of various means as will be recognized by those of ordinary skill in the art, including the use of adhesives, heat welding, stitching, or any of various other means. Because the rear side of the receptacle housing 70 is attached to the fabric of the garment 10, the opposing front side of the receptacle housing 70 faces away from the body of the wearer and is exposed on the outside of the garment 10. The front side of the receptacle housing 70 (as shown in FIG. 6) is more contoured than the rear side and configured to receive and retain the electronics module 22, as explained in further detail below.

With particular reference to FIG. 5, when the electrode lead 50 is positioned in the receptacle housing 70, the rear plate 52 of the electrode lead 50 is exposed on the rear of the receptacle housing 70. The finger 64 extends through a channel 72 in the receptacle housing 70 that curves and generally follows the same contour of the finger 64. The channel 72 does not bore through the receptacle housing 70, but is instead oriented substantially parallel to the generally flat rear surface of the receptacle housing 70. In other words, the channel 72 is elongated in a direction that extends substantially parallel to the rear surface of the receptacle housing 70. The tangs 54 are positioned on the opposite side of the rear plate 52 and are crimped to the electrode 16 in order to attach the electrode 16 to the electrode lead 50, as described above.

The channel 72 in the receptacle housing 70 leads to a cavity 74. One end of a connection pin 80 is positioned in the cavity 74. The connection pin 80 is fixed in place within the receptacle housing 70 and includes a first end 82 and a second end 84 (not shown in FIG. 5). The first end 82 of the connection pin 80 includes a domed surface that extends into the cavity 74. The finger 64 of the leaf spring 60 engages the domed surface on the connection pin 80 within the cavity 74 by abutment but is not attached to the connection pin. The surface of the finger 64 that engages the connection pin 80 is relatively smooth. The combination of the domed surface of the connection pin 80 and the smooth surface of the finger 64 allows the finger to be easily inserted into the cavity 74 and establish a good electrical connection via the abutment between the electrode lead 50 and the connection pin 80. In at least one embodiment, a bumper 76 is positioned in the channel 72. The bumper 76 is integrally formed with the receptacle housing 70 and further helps in directing the finger 64 into proper engagement with the connection pin 80 during assembly of the receptacle 20. Additionally, the bumper 76 helps maintain proper abutment of the finger 64 and the connection pin 80 following repeated vibrations and impacts to the receptacle during use.

Figure 6:
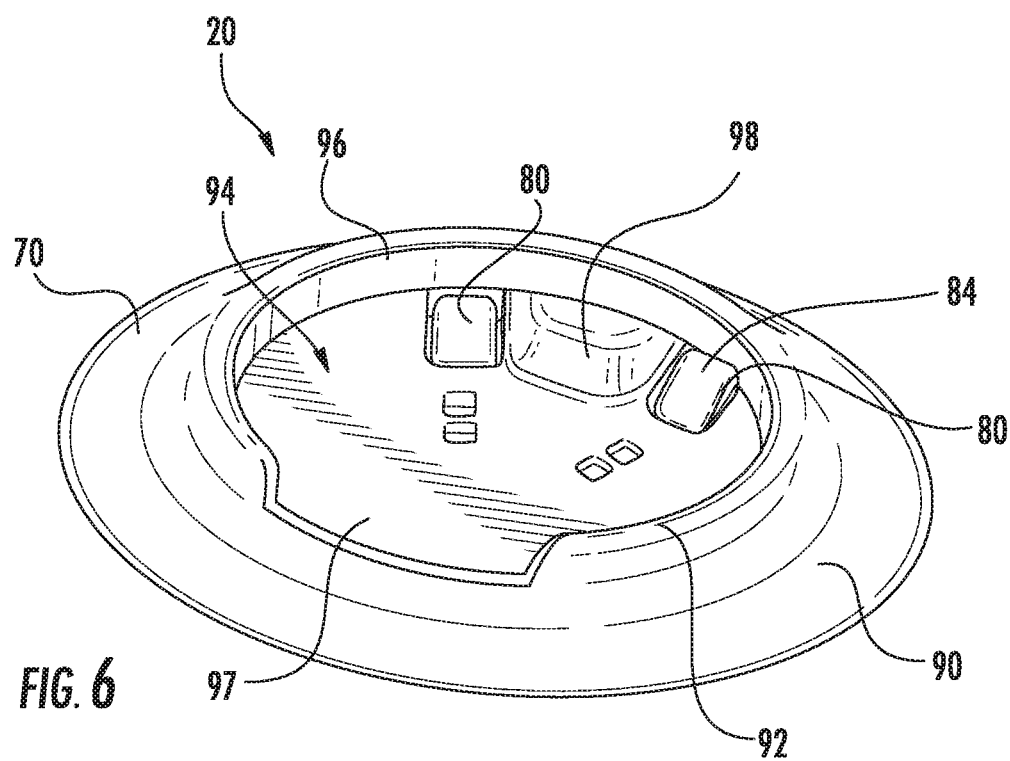
FIG. 6 shows a front perspective view of the receptacle of FIG. 3.

FIG. 6 shows the front side of the receptacle housing 70 (i.e., the reverse side from that shown in FIG. 3). As shown in FIG. 6, the front side of the receptacle housing 70 includes a contoured base 90 with a central perimeter 92. A socket 94 is defined on the front surface of the receptacle housing 70 within the contoured base 90. An entrance to the socket 94 is defined by the central perimeter 92 of the contoured base 90. The central perimeter 92 defines a lip on the receptacle housing 70 with the recess provided by the socket 94 extending behind the lip (i.e., under the lip when the receptacle 20 is viewed from a top position). The socket 94 is further defined by a circular sidewall 96 and a back wall 97 of the socket 94. While the circular sidewall 96 may be formed in a perfectly circular shape, it will be recognized that the term "circular" as used herein simply refers to a curved or annular shape that is substantially circuitous. A detent 98 is positioned in the socket 94. The detent 98 is configured to engage features on the electronics module 22, as explained in further detail below.

The receptacle 20 is configured to receive and retain the electronics module 22 within the socket 94 and also facilitate electrical connection between the electronics module 22 and the electrodes 16 of the sensor arrangement 14. Accordingly, the connection pin 80 that engages the electrode leads 50 within the contoured base 90 also extends into the socket 94. In particular, a second end 84 of each connection pin 80 extends into the socket 94 through an opening in either the sidewall 96 or the back wall 97 of the socket 94. In the embodiment of FIG. 6, the second end 84 of the connection pin 80 is provided on the back wall 97 and at the base of the sidewall 96. Advantageously, this orientation and arrangement of the connection pin 80 allows contacts on the electronics module 22 to make electrical connection with the receptacle 20 without posts or other electrical contact members extending directly into the back wall 97 of the socket and toward the wearer (i.e., the electrical contact members are not perpendicular to the back wall 97 and the chest of the wearer). This provides an added safety feature for the sensor arrangement 14 disclosed herein. Instead of an orientation with an elongated electrical contact being perpendicular to the wearer (and the back wall 97 of the socket 94), the connection pin 80 disclosed herein is substantially parallel to the back wall 97 of the socket 94. Moreover, insertion and removal of the electronics module 22 from the receptacle 20 is made easier in the disclosed embodiment by the design of the electrical contacts near or in the sidewall 96 of the socket 94.

In the disclosed embodiment, the second end 84 of the connection pin 80 that extends into the socket is substantially smooth and flat with a relatively large surface area to facilitate engagement with a contact on the electronics module 22. However, it will be appreciated that in other embodiments the ends of the connection pin 80 may be any of various shapes. Moreover, it will be recognized to those of ordinary skill in the art that the connection pin 80 may be replaced with any other adequate electrical conductor, and need not be provided in the shape of a pin or other post-like member.

The electrode leads 50 may be positioned within the receptacle housing 70 using any of various methods. For example, the electrode leads 50 may be insert molded, press-fit or otherwise molded or inserted into the receptacle housing during manufacture of the receptacle 20. In at least one embodiment, the electrode leads are inserted into the receptacle housing by threading the finger 64 through the associated channel 72 of the receptacle housing 70, past the bumper 76 and into an interference fit with the connection pin 80 in the cavity 74 of the receptacle housing. Thereafter, or before insertion of the finger 64 through the channel 72, the tangs 54 are inserted through the holes 46 in the electrodes 16 and crimped around the electrode material.

Figure 7:
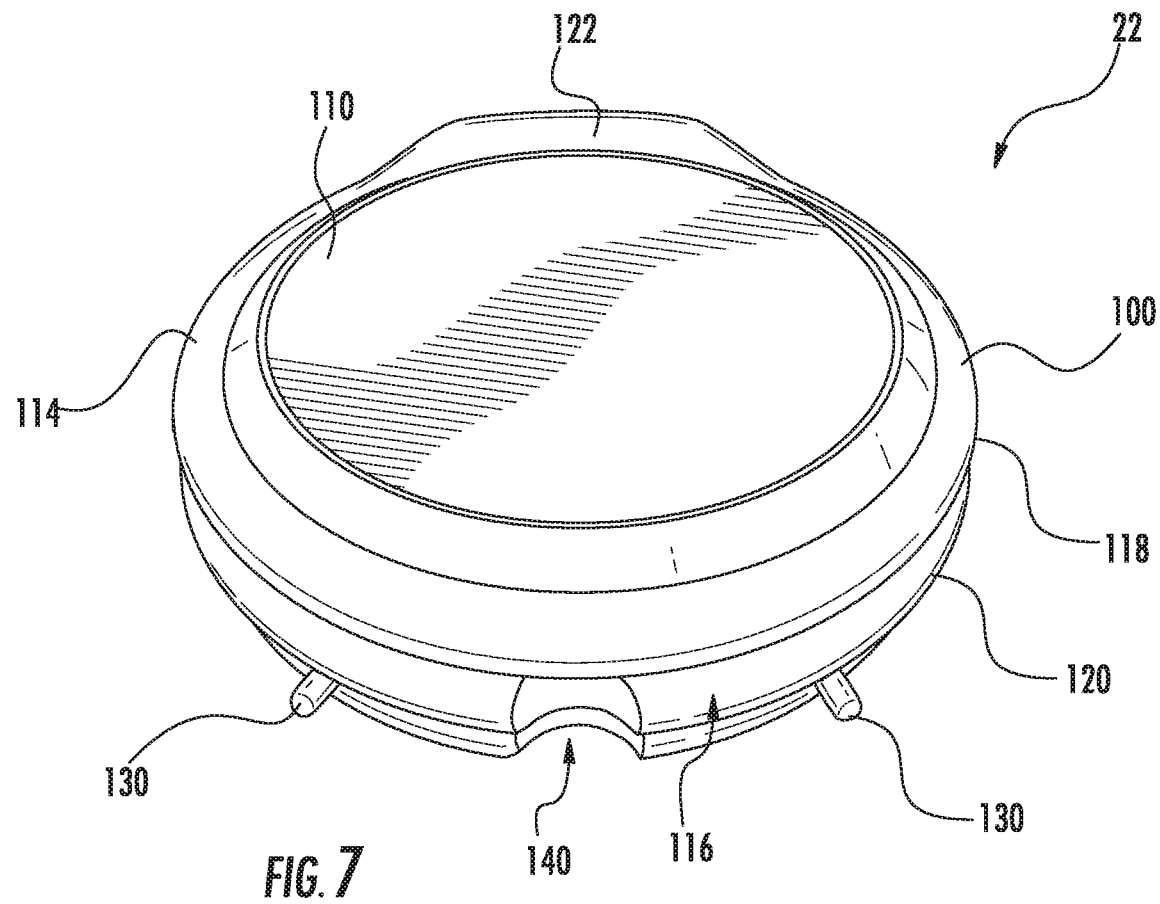
FIG. 7 shows a front perspective view of an electronics module configured for placement in the receptacle of FIG. 6.
Figure 8:
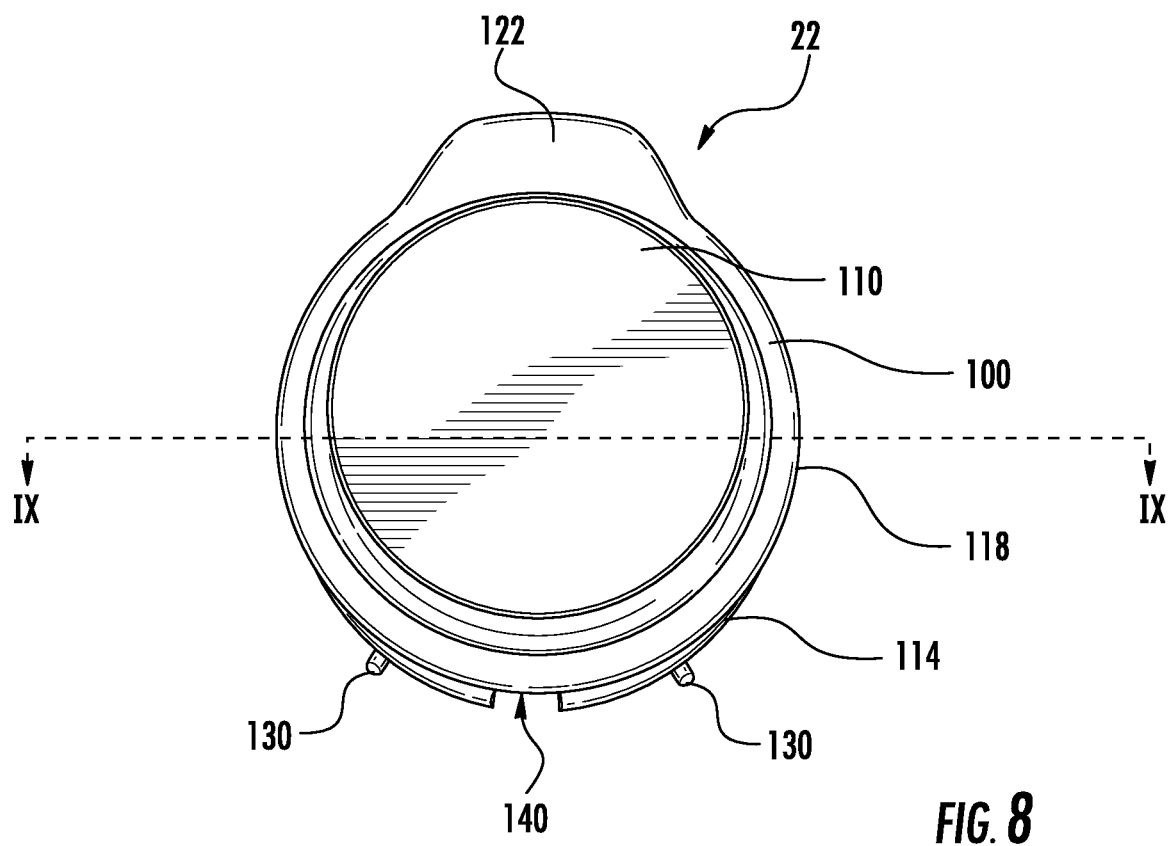
FIG. 8 shows a front view of the electronics module of FIG. 7.
Figure 9:
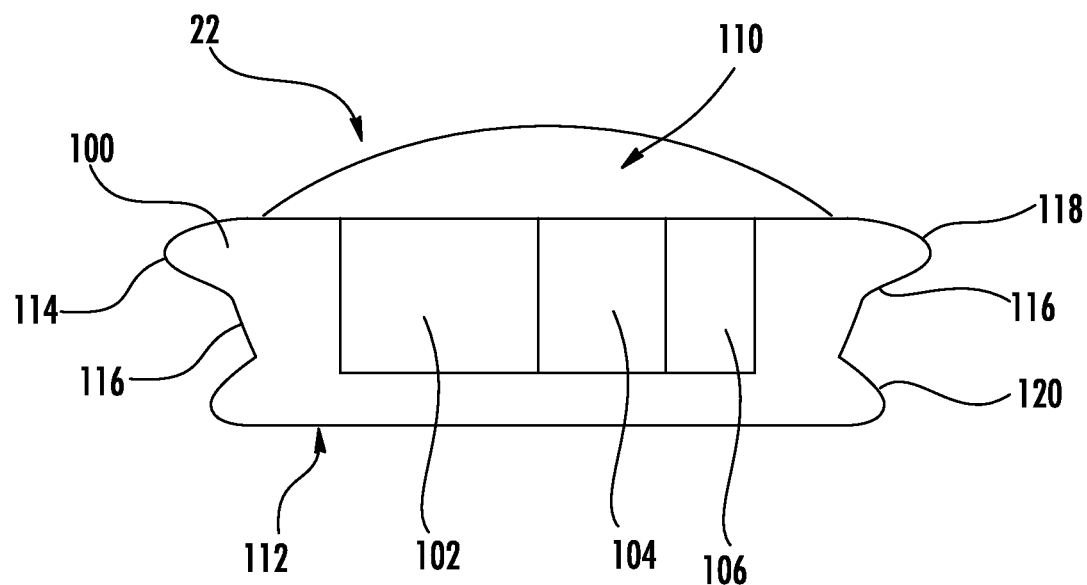
FIG. 9 shows a cross-sectional view of the electronics module through line IX-IX of FIG. 8.

With reference now to FIGS. 7-9, the electronics module 22 is shown. The electronics module 22 includes a microprocessor 102, power device in the form of a power cell 104, and electronic transceiver 106 all contained within a module housing 100. The module housing 100 is generally disc shaped and includes a rounded outer face 110, a substantially flat inner face 112, and a circular sidewall 114 with a medial groove 116. The inner face 112 is configured for insertion into the socket 94 in the receptacle housing 70. The medial groove 116 is defined between an outer rim 118 and an inner rim 120 on the circular sidewall 114. The medial groove 116 is adapted to receive the central perimeter 92 of the receptacle housing 70 when the inner face 112 of the electronic module 22 is inserted into the socket 94. In other words, the central perimeter 92 of the receptacle housing 70 is positioned between the outer rim 118 and the inner rim 120 of the medial groove 116 when the electronics module 22 is seated in the receptacle 20. As a result, the outer face 110 and the outer rim 118 of the electronics module 22 are positioned outside of the socket 94, but the inner face 112 and the inner rim 120 are positioned inside of the socket 94 when the electronics module 22 is seated in the receptacle 20.

With continued reference to FIGS. 7-9, the inner rim 120 of the module housing 100 further includes two contacts 130 that provide an electrical connection to the microprocessor 102 inside the electronics module 22. Each contact 130 is provided as a small pin that extends outward from the inner rim 120 of the circular sidewall 114 on the electronics module 22 and is retained by the module housing 100. The contacts 130 may be spring biased or fixed in place on the circular sidewall. Each contact 130 has a dome shaped end portion that is configured to engage the relatively flat second end 84 of the connection pin 80 in the receptacle 20. As discussed previously, the contacts 130 may be oriented to extend outward from the circular sidewall 114 because of the arrangement of the electrical conductors in the receptacle 20 including the electrode leads 50 and the connection pins 80 that facilitate a sidewall electrical connection to the electronics module 22.

An orientation recess 140 is also provided on the inner rim 120 of the circular sidewall 114 on the electronics module 22. The orientation recess 140 is configured to engage the detent 98 in the socket 94 of the receptacle housing 70 and properly orient the electronics module 22 when it is inserted into the receptacle 20. In particular, when the detent 98 is received within the orientation recess 140, the contacts 130 on the electronics module 22 are properly aligned with the connection pin 80 in the socket 94 of the receptacle 20, and an electronic connection is established between the electronics module 22 and the receptacle 20 and associated electrodes 16.

The outer rim 118 of the electronics module 22 further includes an upper tab 122 designed to facilitate easy removal of the electronics module 22 from the receptacle 20. Because the outer rim 118 is positioned above the central perimeter 92 of the receptacle housing 70, the user may easily engage the rear of the upper tab 122 with his or her finger and force the upper tab 122 away from the receptacle 20. When sufficient force is applied, the medial groove 116 of the module housing 100 is released from the central perimeter 92 of the receptacle housing 70 and the electronics module 22 is dislodged from its seat in the receptacle 20.

The foregoing components provide an improved arrangement and method of creating electrical connections between an electronics package which is removable from a receiver which is non-removably bonded to a shirt or other garment. The foregoing detailed description of one or more embodiments of the garment with an electronic housing and sensor connection arrangement has been presented herein by way of example only and not limitation. It will be recognized that there are advantages to certain individual features and functions described herein that may be obtained without incorporating other features and functions described herein. Moreover, it will be recognized that various alternatives, modifications, variations, or improvements of the above-disclosed embodiments and other features and functions, or alternatives thereof, may be desirably combined into many other different embodiments, systems or applications. For example, various alternative materials may be used in different embodiments of the invention. Additionally, while the receptacle and electronics module have been described herein with respect to a heart rate monitor, it will be appreciated that the arrangement could be used with any different number of sensor arrangements that include or do not include a heart rate monitor. Presently unforeseen or unanticipated alternatives, modifications, variations, or improvements therein may be subsequently made by those skilled in the art which are also intended to be encompassed by the appended claims. Therefore, the spirit and scope of any appended claims should not be limited to the description of the embodiments contained herein.

What is claimed is:

1. A chest strap comprising:
   an elongated fabric portion;
   at least one electrode positioned on the elongated fabric portion;
   a receptacle provided on the chest strap, the receptacle comprising a receptacle housing including a rear surface and a front surface with a socket formed in the front surface, the receptacle further comprising at least one electrode lead retained by the receptacle housing, the at least one electrode lead including a first portion connected to the at least one electrode and a second portion extending through a channel in the receptacle housing, wherein the channel is elongated in a direction that extends parallel to at least a part of the rear surface of the receptacle housing; and an electronics module releasably positioned within the socket, the electronics module including at least one module contact, wherein the at least one module contact is electrically connected to the electrode lead when the electronics module is positioned within the socket.

2. The chest strap of claim 1, the receptacle further comprising at least one receptacle contact engaging the at least one electrode lead, the at least one receptacle contact further engaging the at least one module contact when the electronics module is positioned in the socket.

3. The chest strap of claim 2, wherein the at least one module contact is elongated in a direction that extends parallel to at least the part of the rear surface of the receptacle housing when the electronics module is positioned within the socket.

4. The chest strap of claim 2, wherein the electronics module includes a circular sidewall and the module contact extends outward from the circular sidewall.

5. The chest strap of claim 1, wherein the first portion of the electrode lead includes at least one tang crimped onto the at least one electrode.

6. The chest strap of claim 1, wherein the second portion of the electrode lead includes an elongated finger extending through the channel.

7. The chest strap of claim 6, wherein the receptacle further comprises at least one receptacle contact engaging the electrode lead, and wherein the finger is a curved finger with a smooth surface that engages a domed end of the receptacle contact in a cavity of the receptacle housing.

8. The chest strap of claim 7, further comprising a bumper positioned in the channel, the bumper configured to urge the curved finger into engagement with the domed end of the receptacle contact.

9. The chest strap of claim 1, wherein the electrode lead includes a rear plate positioned against the rear surface of the receptacle housing, the first portion of the electrode lead positioned on one side of the rear plate and the second portion of the electrode lead positioned on an opposite side of the rear plate.

10. A garment comprising:
a body portion;
an electrode positioned on the body portion;
a receptacle positioned on the body portion, the receptacle comprising a housing, an electrode lead, and a receptacle contact, a first portion of the electrode lead extending through a hole in the electrode, a second portion of the electrode lead abutting the receptacle contact such that the electrode lead is electrically connected to the receptacle contact; and
an electronics module releasably positioned in the receptacle, the electronics module including a module contact, the module contact engaging the receptacle contact when the electronics module is positioned in the receptacle to establish an electrical connection between the module contact and the receptacle contact.

11. The garment of claim 10, wherein the body portion is provided on one of a shirt, a chest strap, a bra, or an article of footwear.

12. The garment of claim 10, wherein the body portion is a fabric portion provided on a torso portion of the garment.

13. The garment of claim 10, the second portion of the electrode lead including a finger extending through a channel in the receptacle housing, wherein the channel is elongated in a direction that extends parallel to at least a part of a rear surface of the receptacle housing.

14. The garment of claim 13, wherein the module contact is elongated in a direction that extends parallel to the part of the rear surface of the receptacle housing when the electronics module is positioned in the receptacle.

15. The garment of claim 10, wherein the electronics module includes a circular sidewall and the module contact extends outward from the circular sidewall.

16. The garment of claim 10, wherein the electrode lead includes a tang extending through the hole in the electrode and crimped onto the electrode.

17. The garment of claim 10, wherein the second portion of the electrode lead is a finger engaging the at least one receptacle contact in a cavity of the receptacle housing, the receptacle housing further comprising a bumper configured to urge the finger into engagement with the receptacle contact.

18. The garment of claim 17, wherein the finger is elongated in a direction that extends parallel to at least a part of a rear side of the receptacle housing.

19. A garment comprising:
a sensor;
a body portion;
a receptacle provided on the body portion, the receptacle comprising a receptacle housing, a sensor lead, and a receptacle contact, the receptacle housing forming a socket including a back wall and at least one sidewall, the sensor lead abutting the receptacle contact and retained within a channel extending through the at least one sidewall, the receptacle contact including a contact surface exposed to the socket with the contact surface oriented perpendicular to the back wall of the socket; and
an electronics module releasably positioned within the socket, the electronics module including at least one module contact, wherein the at least one module contact abuts the receptacle contact and is electrically connected to the sensor lead when the electronics module is positioned within the socket.

20. The garment of claim 19, wherein the body portion is provided on one of a shirt, a chest strap, a bra, or an article of footwear.

* * * * *